(12) United States Patent
Weber et al.

(10) Patent No.: US 9,782,285 B1
(45) Date of Patent: Oct. 10, 2017

(54) ELBOW-FOREARM ANTI-ROTATION ORTHOSIS

(71) Applicant: WEBER ORTHOPEDIC, INC., Santa Paula, CA (US)

(72) Inventors: James J. Weber, Santa Barbara, CA (US); Jamie McMillan, Billings, MT (US)

(73) Assignee: Weber Orthopedic, Inc., Santa Paula, CA (US)

( * ) Notice: Subject to any disclaimer, the term of this patent is extended or adjusted under 35 U.S.C. 154(b) by 299 days.

(21) Appl. No.: 14/341,654

(22) Filed: Jul. 25, 2014

Related U.S. Application Data

(60) Provisional application No. 61/883,826, filed on Sep. 27, 2013.

(51) Int. Cl.
    *A61F 5/00*     (2006.01)
    *A61F 5/01*     (2006.01)

(52) U.S. Cl.
    CPC .................................. *A61F 5/0118* (2013.01)

(58) Field of Classification Search
    USPC ........................ 602/4, 5, 20, 21, 60–64, 22
    See application file for complete search history.

(56) References Cited

U.S. PATENT DOCUMENTS

| | | | |
|---|---|---|---|
| 1,643,850 A * | 9/1927 | Jones .................. | A61F 5/05858 602/16 |
| 4,235,228 A | 11/1980 | Gaylord et al. | |
| 5,456,659 A * | 10/1995 | Gildersleeve ....... | A61F 5/05841 602/15 |
| 7,314,457 B2 | 1/2008 | Reaux | |
| 7,329,229 B2 | 2/2008 | Scheinberg | |
| 7,988,653 B2 | 8/2011 | Fout | |
| 8,608,677 B2 * | 12/2013 | Motyer ................. | A61F 5/0111 128/878 |
| 2003/0078530 A1 * | 4/2003 | Wolfe ................... | A61F 5/0118 602/21 |
| 2004/0002671 A1 | 1/2004 | Reaux | |
| 2005/0234374 A1 * | 10/2005 | Grim ................... | A61F 5/05841 602/6 |
| 2009/0293884 A1 * | 12/2009 | DaSilva ................ | A61G 13/12 128/845 |
| 2010/0210985 A1 * | 8/2010 | Kuorak ................. | A61F 5/3723 602/20 |

(Continued)

FOREIGN PATENT DOCUMENTS

EP            0439552 B1     3/1995

*Primary Examiner* — Kim M Lewis
(74) *Attorney, Agent, or Firm* — Paul Y. Feng; One LLP

(57) ABSTRACT

An elbow-forearm anti-rotation support system and process that do not require a hardenable material. The system includes an orthopedic support such as a wrist-hand orthosis, wrist-hand-thumb orthosis, or cast, joined to a bottle-shaped forearm wrap with opposed flaps formed into a clamshell. Proximal elbow flaps include a center elbow region that extends from the proximal end of the forearm wrap. A U-shaped reinforcement stay is disposed on the center elbow region and attaches to the forearm flaps. Cross straps extending from the proximal elbow flaps attach to the forearm flaps, and a closure strap secures the two flaps together. Hook and loop fasteners extending from the distal edge of the forearm wrap attach the forearm wrap to the orthopedic support.

17 Claims, 11 Drawing Sheets

(56) References Cited

U.S. PATENT DOCUMENTS

| | | | |
|---|---|---|---|
| 2010/0217168 A1* | 8/2010 | King | A61F 5/0118 |
| | | | 602/21 |
| 2012/0184887 A1* | 7/2012 | Wynne | A61F 5/0111 |
| | | | 602/19 |
| 2012/0215146 A1* | 8/2012 | Dao | A61F 5/0118 |
| | | | 602/20 |
| 2013/0211304 A1 | 8/2013 | Romo | |
| 2013/0296757 A1* | 11/2013 | Kaphingst | A61F 5/013 |
| | | | 602/20 |

* cited by examiner

ELBOW-FOREARM ANTI-ROTATION ORTHOSIS

CROSS-REFERENCE TO RELATED APPLICATIONS

This application claims priority to U.S. provisional patent application No. 61/883,826, filed Sep. 27, 2013, by the same inventors, the contents of which are incorporated by reference.

FIELD OF THE INVENTION

The present invention relates to an orthopedic brace. In particular, the present invention relates to an elbow-forearm anti-rotation orthosis to immobilize the elbow and wrist or like injuries.

BACKGROUND

A "Sugar Tong" splint is a splint that is used to immobilize both lower arm bones so there is no motion relative to themselves—in other words an anti-rotation splint of the forearm. The indications for these types of splints are: distal radius or ulna fractures, and fractures of the wrist and elbow. Advantages of the splint are that it greatly restricts rotation of the forearm—supination and pronation of the forearm—while allowing for swelling and providing excellent strength. The name of the splint is derived from its appearance which is reminiscent of sugar tongs used to pick up cubes of sugar.

One of the disadvantages of this conventional sugar tong splint is the time involved and skilled technique required to properly make the splint and apply it to the patient. For example, each sugar tong splint is custom made to fit each patient using components such as adhesive tape, gauze, strips of casting tape, and bandage, which then must be cut to size with scissors and pieced together. Strips of splint or casting material must be selected for the correct dimensions and its length cut to match the patient's arm, moistened sufficiently but not overly, applied precisely to the patient's wrist/forearm/elbow regions, leaving gaps in key areas to accommodate for swelling. The technician must also carefully wrap and smooth out folds and creases, etc., to ensure efficacy and comfort for the patient.

The splint typically includes or is impregnated with hardenable material such as plaster, fiberglass, resin, etc. Thus, applying the splint to the patient correctly and doing so before the hardenable material begins to set, cure, or harden involves a time constraint. Due to this time constraint, once the hardenable material sets, cures, or hardens, no further adjustments can be made to accommodate for increase or decrease in swelling, to increase range of motion of the injured joint, to enable exercising the injured limb, to remove creases or smooth out bunched material, etc.

Thus, having an off-the-shelf bracing system ready to go offers greater ease and flexibility to doctors, cast technicians, and therapist to treat arm fractures more efficiently and effectively at the hospital, clinical, and therapeutic levels.

SUMMARY OF THE INVENTION

The present invention in a preferred embodiment is directed to an elbow-forearm anti-rotation support system that does not use hardenable material. As seen in FIG. 1, a preferred embodiment sugar tong forearm brace comprises a forearm wrap 1 that may or may not be split down the center with stretch material and secured with flexible fabric 1a. The forearm wrap 1 is made of either a flexible semi-rigid material, or a soft pliable material and has two opposed flaps or panels 9. The distal edge of the forearm wrap 1 has connective means 2 (e.g., hook and loop fasteners, or like attachments) to secure the sugar tong brace to any of the following: (a) wrist-hand orthosis shown in FIG. 1; (b) wrist-hand-thumb orthosis (thumb spica splint); (c) short arm cast; (d) thumb spica cast; or (e) similar orthopedic brace, support, splint, or cast.

In the preferred embodiment, the proximal end of the forearm wrap 1 is tapered or bottlenecked to seat at the elbow of the patient, with proximal flaps 3 that come up the back of the upper arm and wrap around the sides of the back of the lower part of the upper arm. Straps 4 are connected to the end of each flap 3 (and can be connected pivotally, they are sewn in this prototype) and cross over the top of the forearm and secure on opposite sides of the forearm with hook means 5. An inner removable malleable aluminum stay 6 with attachment means at each end 7 is secured to the inside back portion of the proximal wrap flaps 3. The malleable aluminum strip is designed to be shaped around the back just above the elbow. A closure strap 8 is also attached to the forearm wrap 1 to assist with initial application. Removable lateral and medial stiffeners are placed inside of pockets that are sewn to the outside of forearm wrap 1, for increased stiffness and support.

DETAILED DESCRIPTION OF THE PREFERRED EMBODIMENTS

Conventional sugar tong casts or splints are used to stabilize injuries of the forearm and wrist by preventing forearm rotation and wrist motion. These casts and splints may further be used to maintain alignment of broken bones or to protect a patient's forearm or wrist after surgery. A conventional sugar tong cast is made from plaster, fiberglass, or like hardenable splinting material, usually in the form of 3-inch or 4-inch wide strips. A skilled technician applies the strips to the patient with his or her palm down on the forearm behind the humerus and back to the top of hand like a stirrup. The present invention system completely replaces the conventional sugar tong cast that must be custom made from strips impregnated with hardenable material.

Figure 1:
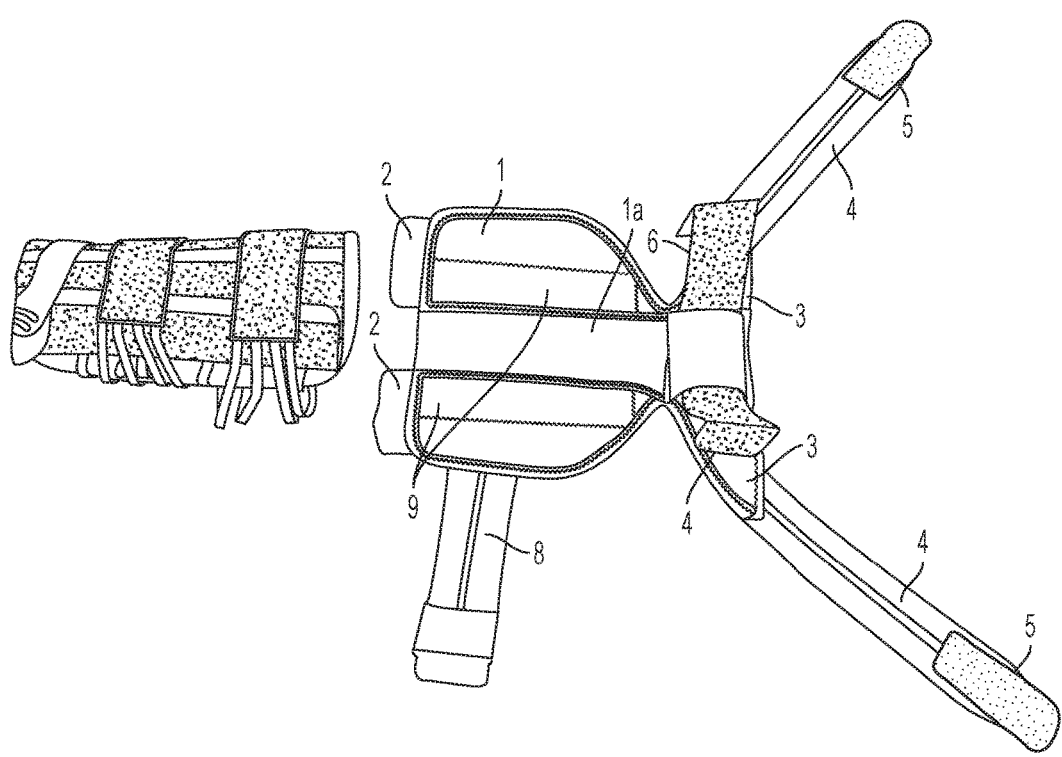
FIG. 1 is a plan view of an elbow-forearm anti-rotation support system.

FIG. 1 is a preferred embodiment of the present invention an elbow-forearm anti-rotation support system, also known as a sugar tong brace. In particular, the present invention in the preferred embodiments is directed to an orthopedic support such as a wrist/hand, or wrist/hand/thumb forearm elbow orthosis joined to a forearm-elbow portion with minimal to no relative rotation therebetween. The forearm-elbow portion of the brace may be further used in concert with a short arm cast or splint, or thumb spica cast or splint. The preferred embodiment shown in FIG. 1 is a sugar tong forearm brace used optionally in combination with a wrist-hand orthosis.

Figures 5A, 5B:
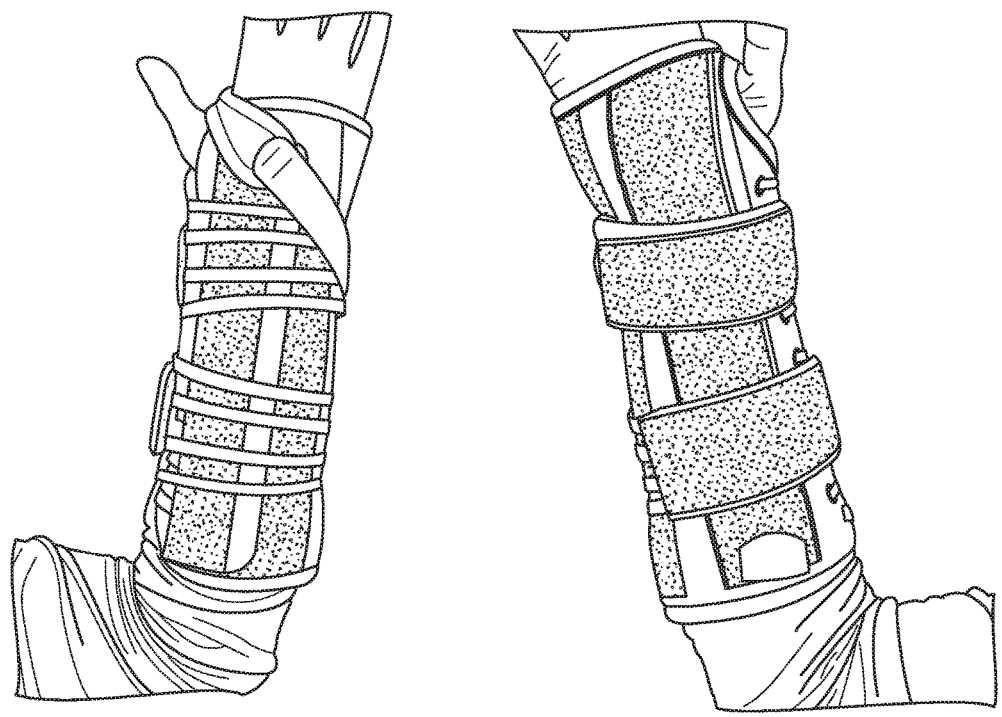
FIGS. 5A and 5B are side elevational views of the lateral and medial sides, respectively, of the wrist-hand orthosis worn on a patient's arm.

FIGS. 1, 5A, and 5B show an exemplary embodiment orthopedic support, here, a wrist-hand orthosis. It is made from a flexible holder to receive the patient's wrist, and has two flaps that close toward one another to secure the holder about the patient's wrist and forearm. Tightening strands, straps, or laces pass through the edges of the flaps to cinch up the two flaps, and anchoring flaps at the collective ends of the laces attach to the brace once the flaps are tightened. Another strap extends over the base of the thumb as with a thumb spica splint. The exterior of the flaps is made of a UBL (unbroken loop) or like material for easy attachment for hook and loop fasteners or the like.

In the embodiment shown in FIGS. 1, 5A, and 5B, the wrist-hand orthosis connected to the forearm wrap 1 may be of the type disclosed in, for example, U.S. Pat. No. 6,893, 410 (Helv) and U.S. Pat. No. 6,960,176 (Helv et al.), which contents are incorporated by reference. Aside from the wrist-hand orthosis of FIGS. 1, 5A, and 5B, other orthopedic supports, braces, splints, are contemplated, such as: a wrist cast, short arm cast, thumb spica cast, wrist-hand orthosis, or wrist-hand-thumb orthosis known in the art; braces and splints disclosed on applicant's website: http://www.helyweber.com/index.php/upper-extremities/wrist-hand-a-thumb; or, for example, U.S. Pat. Nos. 7,033,331; 7,056,298; 6,142,966; 7,278,980; 7,442,177; 7,455,650; 7,402,149; 7,276,039; and 7,713,223, the contents of all of which are incorporated by reference.

Figure 3:
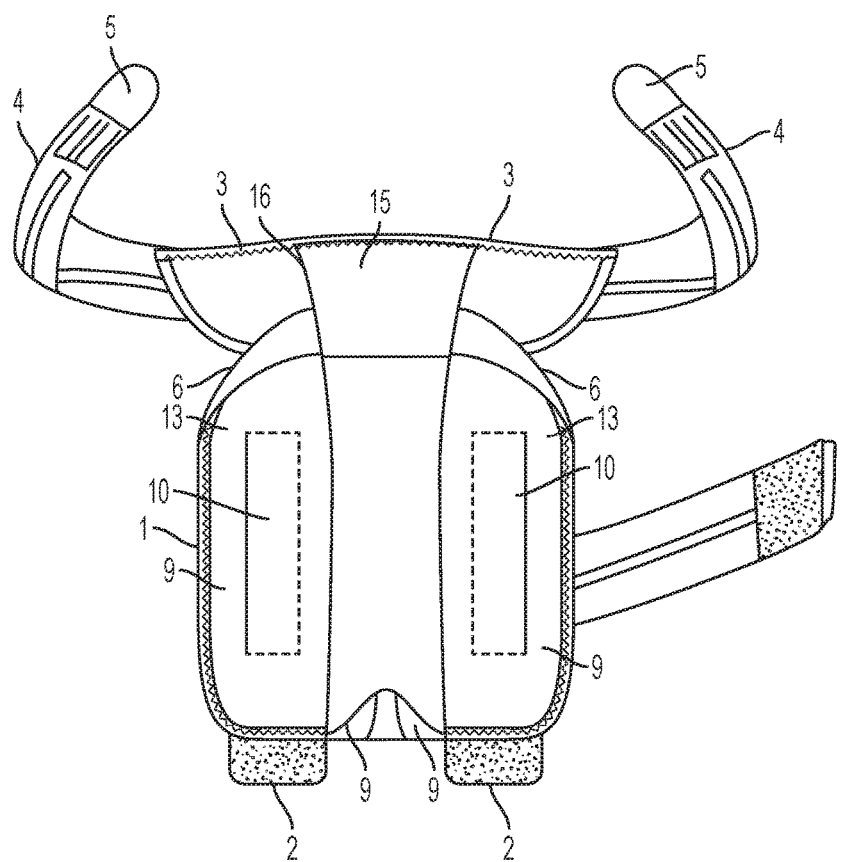
FIG. 3 is a plan view of a preferred embodiment sugar tong forearm wrap/portion.
Figure 10:
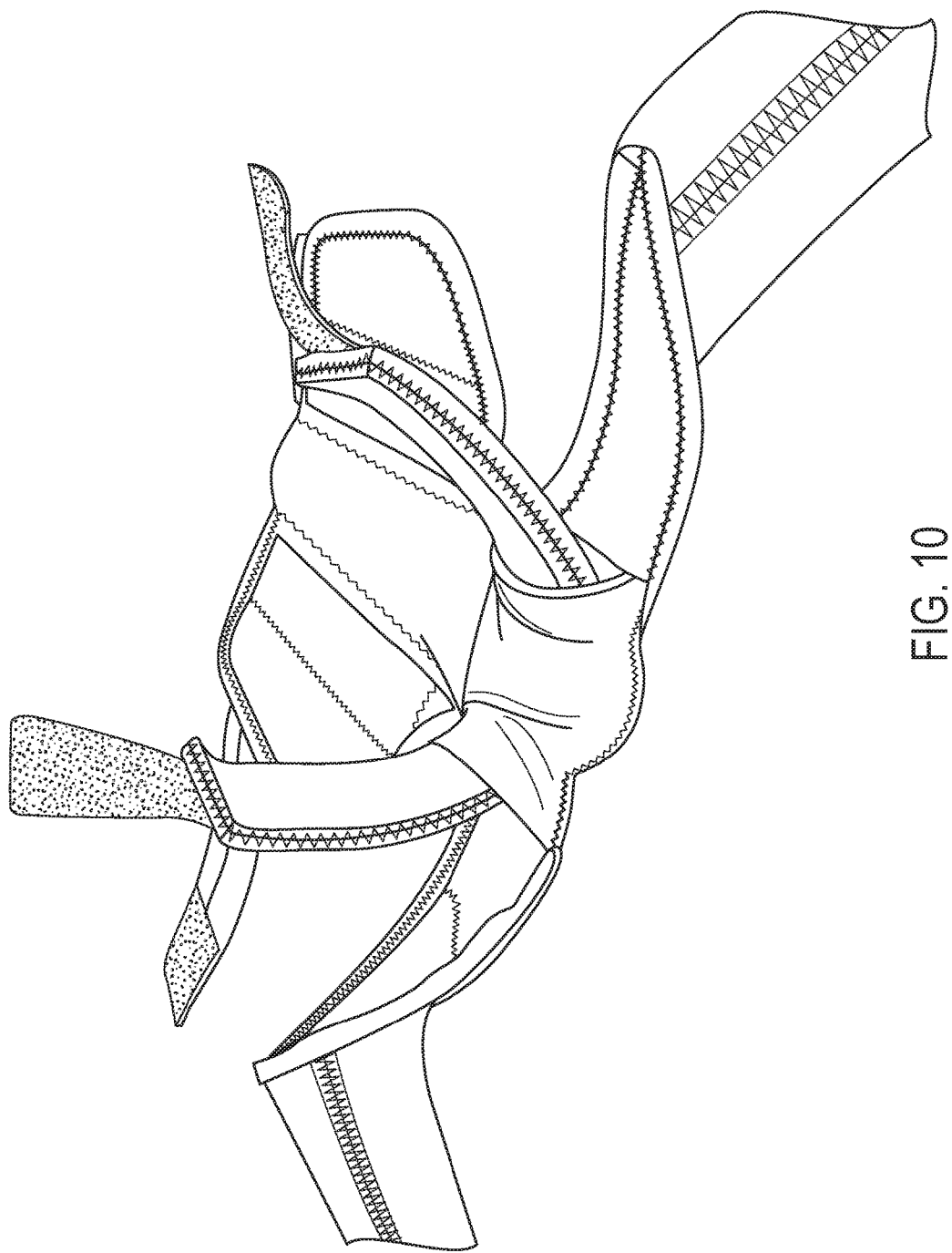
FIG. 10 is the preferred embodiment forearm wrap/portion showing the interior, with the first and second forearm flaps laid open, a U-shaped reinforcement stay, and proximal elbow flaps with straps laid open.
Figure 11:
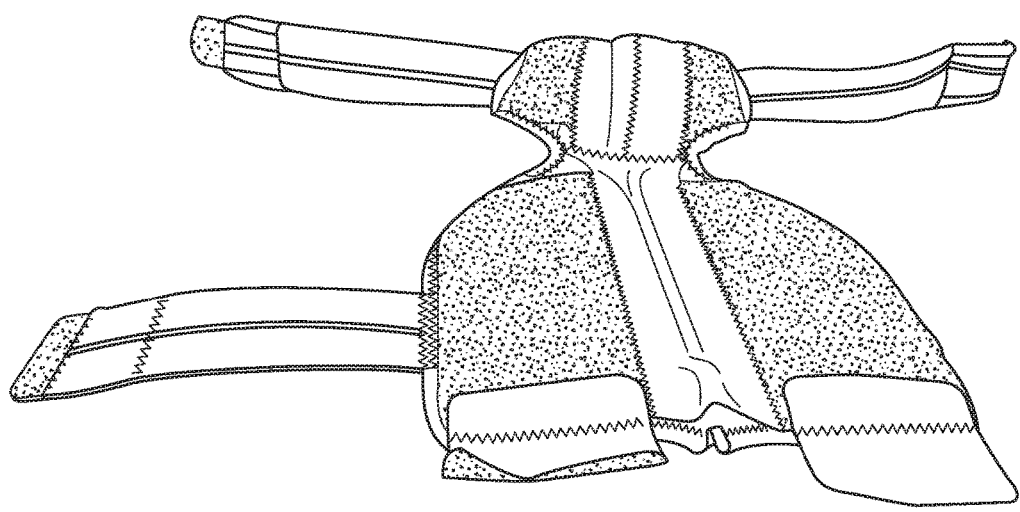
FIG. 11 shows the exterior of the forearm wrap/portion from FIG. 10.
Figure 12:
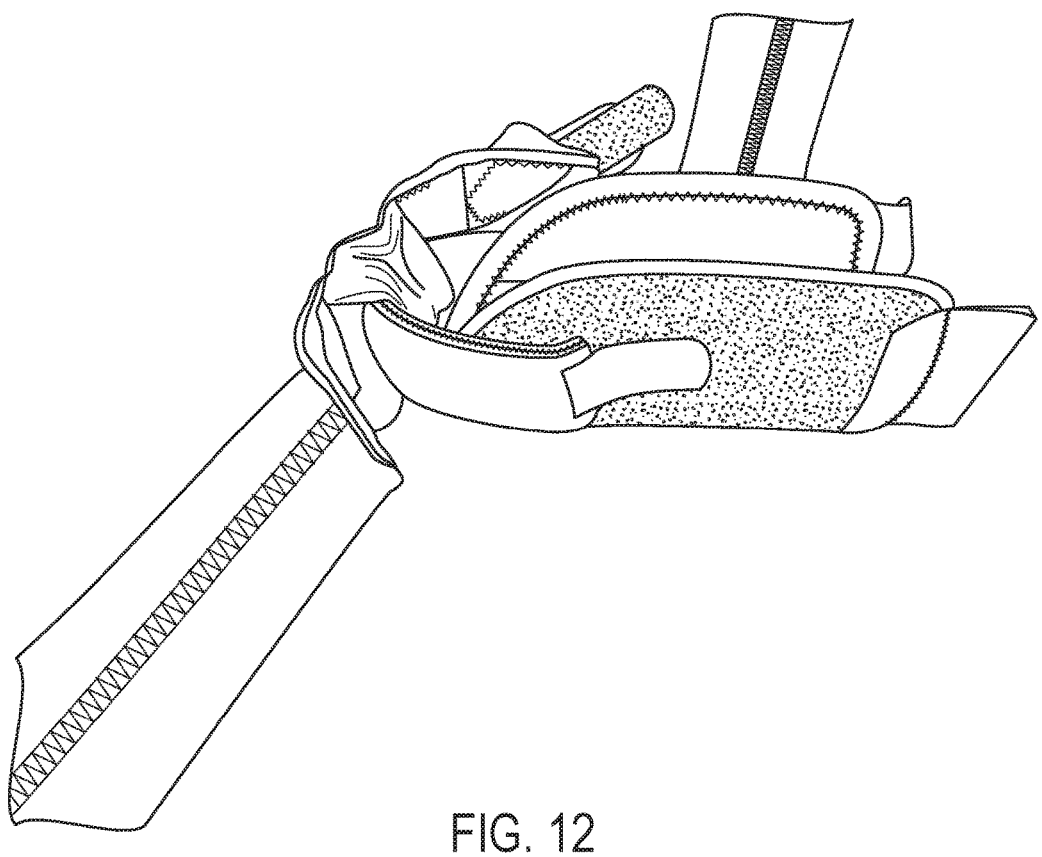
FIG. 12 is a side elevational view of the forearm wrap/portion from FIG. 10 with the proximal-elbow end on the left side and the distal-wrist end on the right side.

FIG. 3 is a plan view of a preferred embodiment sugar tong forearm brace depicted in FIG. 1, spread open exposing the interior, and oriented with the proximal or elbow end at the top and the distal or wrist end at the bottom. See also FIGS. 10-12 depicting the forearm wrap 1. The forearm wrap 1 has opposed flaps 9 that include elongated, padded panels shown in the opened position to receive the patient's forearm. The exterior of the panels/flaps 9 preferably include swatches or entirely of UBL or hook and loop fastener material (e.g., VELCRO®) to allow for attachment of VELCRO® hooks, straps, closures, clasps, buckles, claws, and the like. The two panels/flaps 9 are joined along one edge with one or more sheets of elastic fabric acting as an expandable hinge, and when applied, the opposite edges approach each other as in a clamshell leaving a split along the center with no gap, or there may be a gap at the split, or the edges may overlap and fully circumscribe the patient's forearm. In an alternative embodiment, the two flaps 9 may be formed into a cylinder, with elastic expansion regions, to fully circumscribe and enclose the forearm. The flaps 9 is preferably reinforced inside its outer shell with plastic, aluminum, steel, or like stiffener strips 10 for improved rigidity and support for the patient's injured forearm or wrist. The stiffener strips 10 may be stitched or embedded into the flaps 9, or the flaps may include user accessible pockets that receive the stiffener strips inside. An optional soft fabric lining 12 covers the seam between the opposed flaps 9. This minimizes abrasion to and improves the comfort for the wearer's forearm.

Preferred construction materials for the forearm wrap include rigid EVA (ethylene vinyl acetate) foam or other semi-rigid thermoplastic foam with fabric laminated to both sides of the flaps 9. The outer sides of the flaps 9 preferably have a UBL (unbroken loop) fabric that can receive VEL-CRO® hooks, or have added loops to make it VELCRO® hook receivable. There are optional pockets or compartments for one or more plastic or metal (aluminum) stiffeners 10 on one or both sides of the forearm wrap 1. The plurality of stiffeners 10 embedded within the flaps 9 preferably extend substantially the entire length of the forearm wrap 1. Thus, the stiffeners 10 further improve torsional stability of the forearm wrap 1 and of the entire brace.

In an alternative embodiment, the forearm wrap is made from a laminate with semi-rigid EVA foam on both sides of a malleable aluminum (aluminum in the middle to help retain a molded shape) with fabric on both outer sides of the EVA foam. So a laminated forearm wrap would be constructed with the following: fabric (UBL or other), EVA foam or other semi rigid foam, aluminum (malleable) strip(s), EVA foam or other semi rigid foam, fabric (UBL or other). The laminate panels may be glued, stitched, sewn, welded or likewise joined together.

Figure 4:
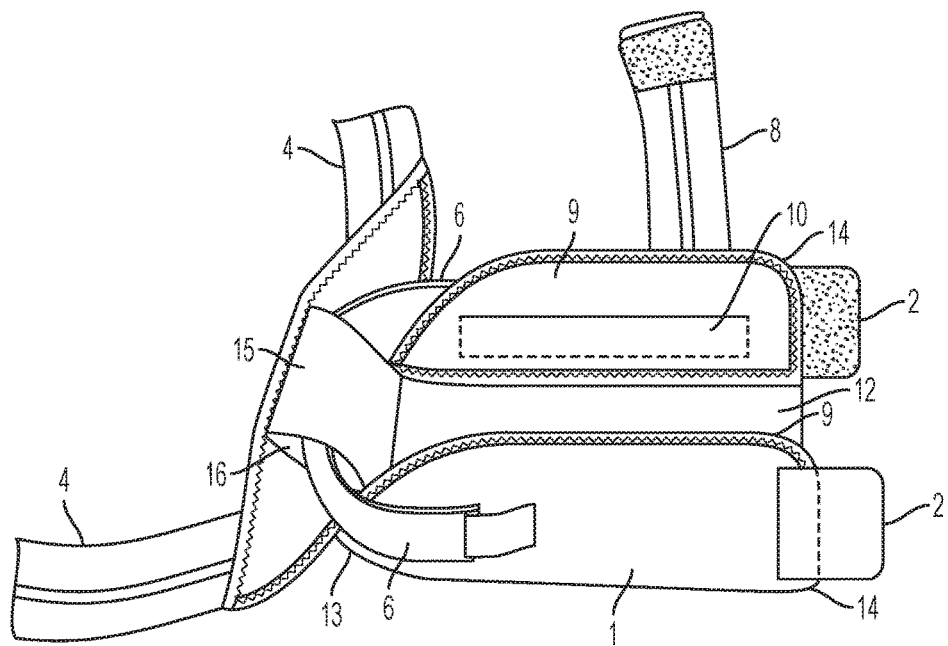
FIG. 4 is a side elevational view of the sugar tong forearm wrap/portion of FIG. 3.

FIG. 4 is a side elevational view of the forearm wrap 1 from FIGS. 1 and 3. As seen in FIGS. 1, 3 and 4, the flaps 9 of the forearm wrap 1 when laid open preferably form a bottleneck shape, with a tapered, narrower proximal edge 13 and a wider distal edge 14. The bottleneck shape minimizes bunching of flap material at the patient's elbow. The proximal edge 13 transitions into proximal flaps 3 that appear as wings extending from a center region covering the patient's elbow. Other shapes are contemplated for the forearm wrap, including a simple rectangle or like polygon.

The distal ends of the proximal flaps 3 each has a respective cross strap 4 used to wrap around the patient's forearm. When the brace is properly applied, the patient's elbow is covered by the soft fabric lining 12, then by the U-shaped reinforcement stay 6, then by the center region of the proximal flaps 3, all of which are secured in place by the cross straps 4. There may be fewer or more than the two cross straps 4 shown. The cross straps 4 are of sufficient length to attach to the exterior of the flaps 9 and/or attach to the wrist-hand orthosis (shown in FIG. 1). The cross straps 4 may have sufficient length to at least partially wind about the forearm wrap 1, further bolstering support for the patient's injured forearm and stabilizing the elbow. These straps use preferably VELCRO® hooks to attach to the forearm wrap 1 and/or the wrist-hand orthosis.

As shown in FIGS. 3 and 4, the sheet of soft fabric lining 12 extends over the center region of the proximal flaps 9 and forms a pocket 15 that receives the patient's elbow therein. Further, the pocket 15 contains a passage 16 that allows an optional U-shaped reinforcement strip or stay 6 to loosely pass through it or be affixed to it, which passage 16 also helps keep the stay 6 in place. The U-shaped reinforcement stay 6 generally has a curved vertex extending into straight legs. The U-shaped reinforcement stay 6 is preferably made from a UBL fabric covering a fairly rigid metallic strip made from aluminum or steel, but plastic may be used too. The metallic strip is somewhat pliable for some level of customized fit for the patient's elbow region, but generally maintains its shape in use. It is fully enclosed or partially covered by a UBL soft fabric, padded, and is intended to provide support and protection for the patient's elbow. The distal ends of the straight legs of the U-shaped reinforcement stay 6 include optional hook and loop fasteners (e.g., VELCRO®) that attach to the exterior of the forearm panels/flaps 9.

An optional closure strap 8 extends from one of the forearm flaps 9 across the split or overlap and to the opposite forearm flap 9 to attach to the exterior thereof, preferably via hook and loop fasteners. More closure straps may be added for longer and larger sized forearm wraps. The strap may be replaced by or complemented by a plurality of laces extending from one flap over the split or gap and joined at the opposite end by a common attachment pad covered with VELCRO® hook fasteners.

All straps 4, 8 are preferably padded and made from soft fabric. Their lengths are preferably inelastic, but elastic straps that compress the forearm are contemplated in alternative embodiments. The ends of the straps 4, 8 are sewn to the base structure and the free distal ends of the straps are anchored to their intended attachment surface via hook and loop fasteners, but hooks, buckles, buttons, snaps, D-rings, laces and eyelets, and the like or any combination thereof, are contemplated.

Figure 6:
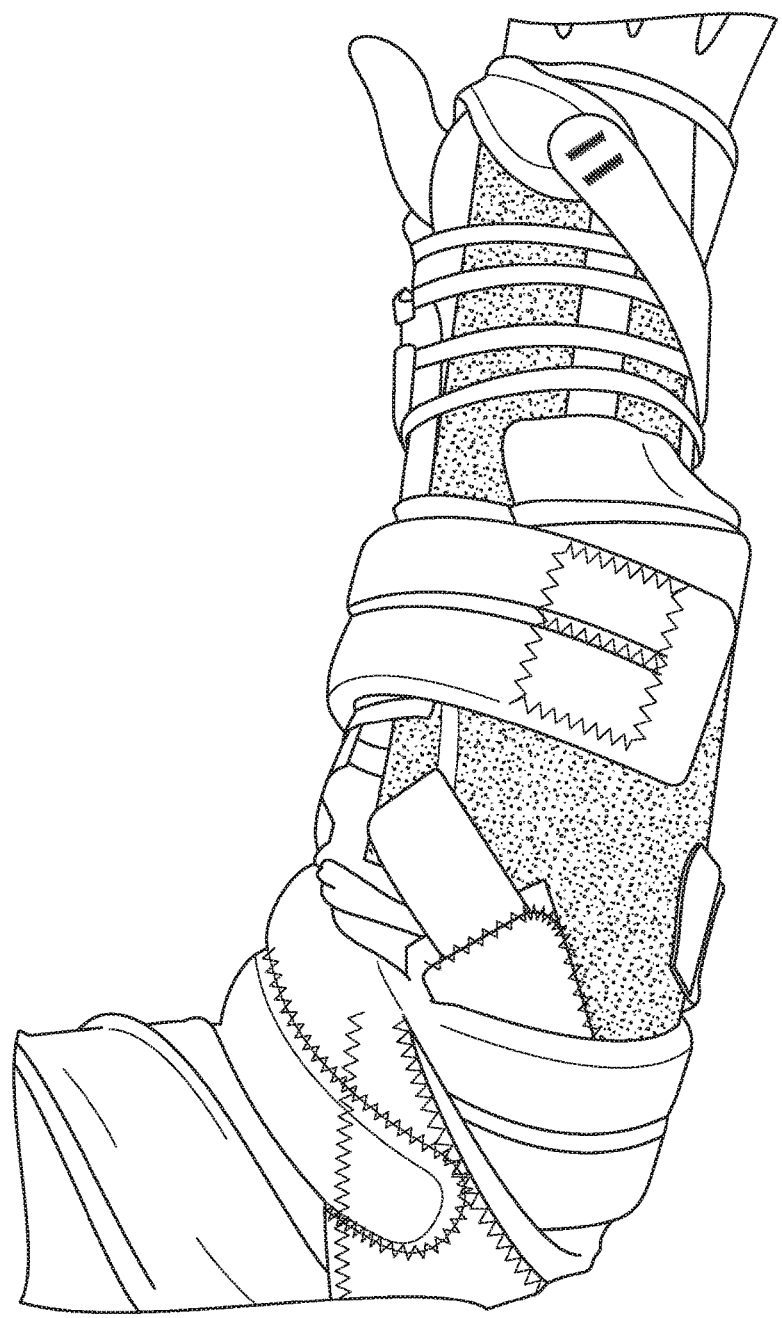
FIGS. 6 and 7 are side elevational views of the lateral and medial sides, respectively, of the wrist-hand orthosis and sugar tong forearm wrap/portion joined together as a system.
Figure 7:
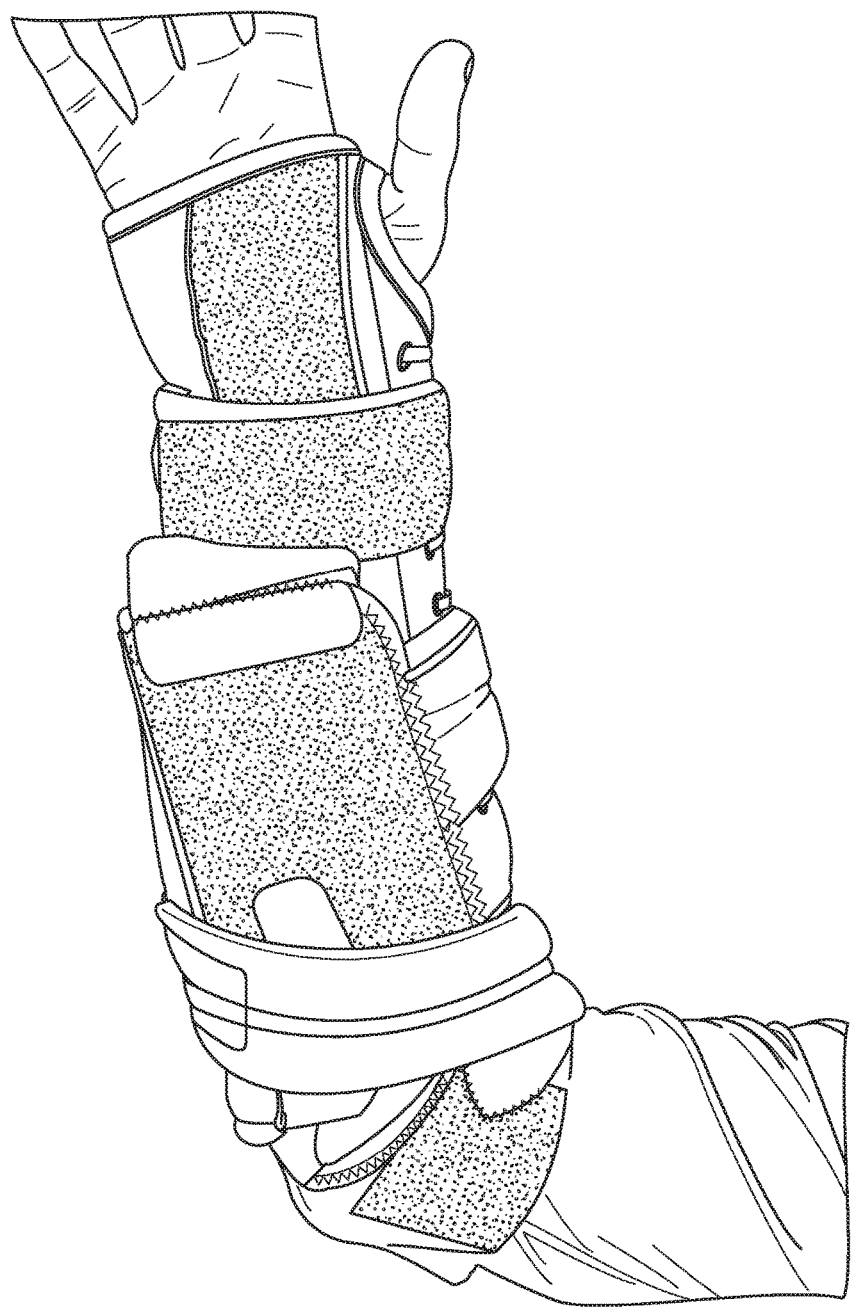
Figure 8:
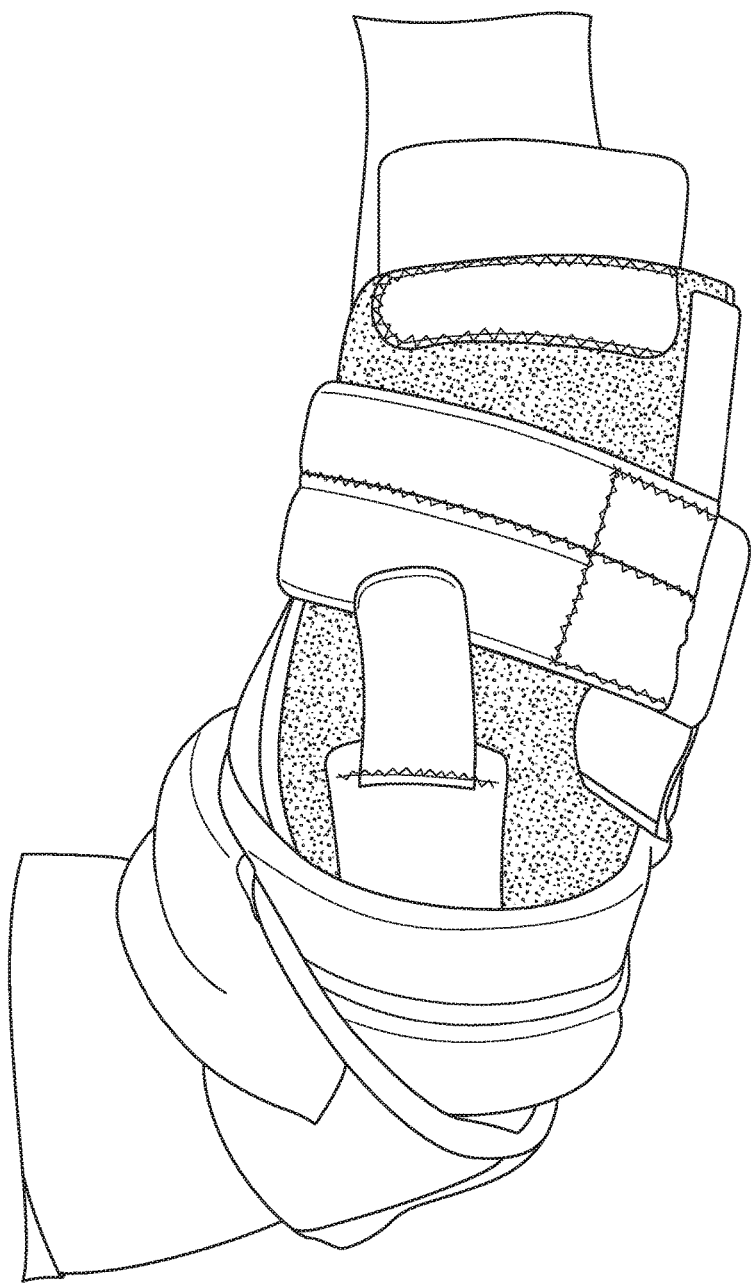
FIG. 8 is a lateral view of the preferred embodiment sugar tong forearm wrap/portion by itself.
Figure 9:
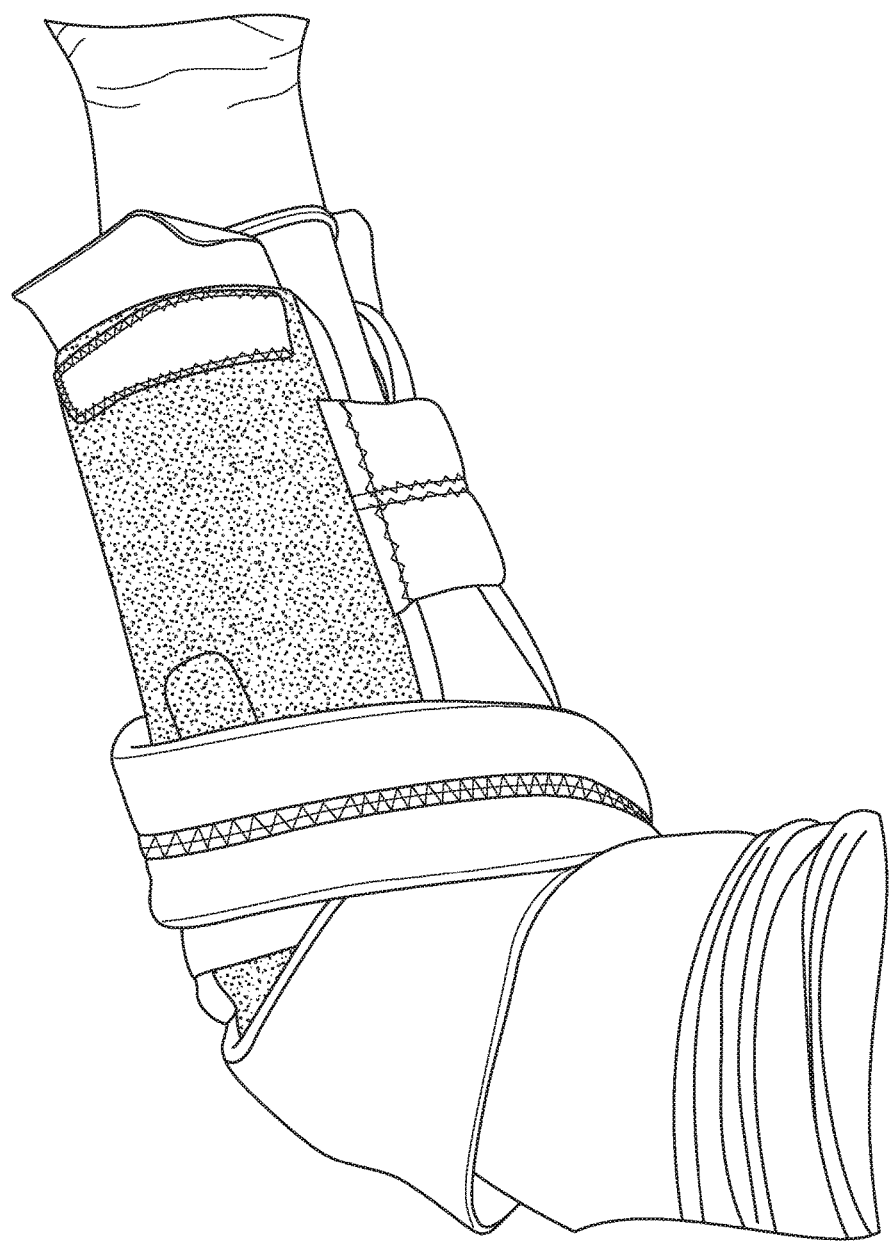
FIG. 9 is a medial view of the forearm wrap/portion from FIG. 8.

As seen in FIGS. 1, 3, 4, 8, and 9, the respective distal edges 14 at the distal end of the forearm flaps 9 preferably include anti-rotation connective means 2 used to join or attach the forearm wrap 1 to the orthopedic support, wrist-hand orthosis, cast, or splint being used (see FIGS. 6, 7). The connective means 2 are preferably two or more panels of VELCRO® hook fasteners that attach to the complementary hook and loop or UBL material or like receiving structure on the wrist-hand orthosis, cast, or splint. The connective means 2 are preferably of sufficient size to minimize the chance of accidental disconnection between the two braces.

Further, the anti-rotation connective means 2 should have sufficient purchase of the wrist-hand orthosis, cast, or splint to minimize relative rotation between the two braces. If hook and loop fasteners are used, they should preferably be large panels for a positive contact to the splint or cast that resists and immobilizes twisting in the patient's forearm and wrist. This feature thus limits the amount of forearm pronation or supination to help with rehabilitation. Instead of hook and loop fasteners, the connective means in alternative embodiments may be snaps, laces and eyelets, D-rings, hooks, zippers, buckles or catches with belts, and the like, or any combination thereof.

Beneficially, the preferred embodiments of the forearm wrap 1 and its components and attachments shown in FIGS. 3, 4, and 10-12, do not require any hardening material (e.g., plaster, resin, fiberglass, etc.) used in a traditional sugar tong cast to create the needed rigidity, anti-rotation, and support. Further, a high level or technician expertise is not required since customized taping and shaping are not required when using the present invention elbow-forearm anti-rotation support system.

FIGS. 2A-2F show a preferred application procedure for the present invention sugar tong brace to a patient's injured forearm.

Figure 2A:
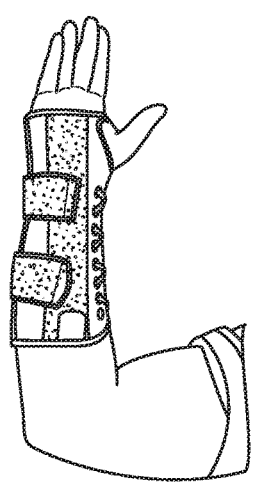
FIGS. 2A-2F show application of the system from FIG. 1 to a patient's arm.

FIG. 2A. Step 1—Apply an orthopedic support such as a forearm cast with a thumb spica cast or thumb spica wrist splint to the patient's forearm and hand.

Figure 2B:
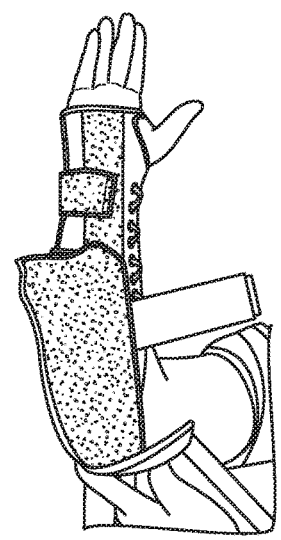

FIG. 2B. Step 2—The patient's forearm is placed inside the forearm wrap. The patient's elbow is seated in the U-shaped reinforcement stay, and the two ends of the stay are attached to the exterior of the wrap using VELCRO® hooks. The stay has an internal U-shaped stiffener that is generally stiff but still somewhat malleable and is adjusted for a customized fit to the patient's elbow.

Figure 2C:
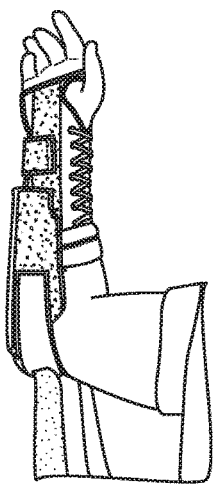

FIG. 2C. Step 3—Attach the anti-rotation connective means of the forearm wrap to the forearm cast or wrist splint, and secure the two sides of the forearm wrap with the closure strap.

Figure 2D:
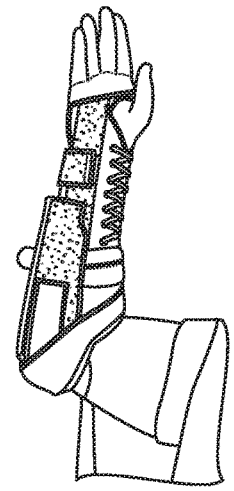

FIG. 2D. Step 4—Secure a first cross strap of the forearm wrap across top of forearm and connect to the forearm cast or wrist splint.

Figure 2E:
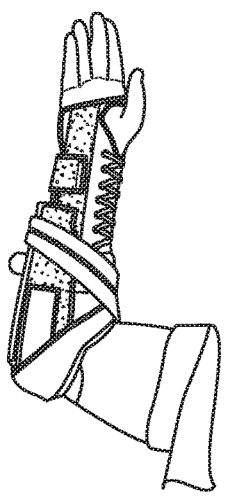

FIG. 2E. Step 5—Secure a second cross strap of the forearm wrap across the top of forearm and secure to the forearm cast or wrist splint.

Figure 2F:
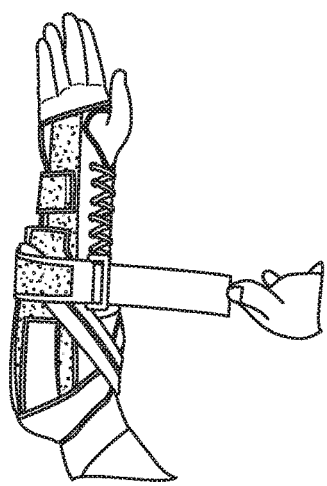

FIG. 2F. Step 6—An additional circumferential closure strap that is discrete from the forearm wrap is applied to the wrap for increased support.

It is contemplated that the patient may already be fitted with a wrist cast, short arm cast, thumb spica cast, or the like. So the patient can wear the existing cast and be fitted with the present invention sugar tong brace as described above. To do this, hook and loop fasteners or mechanical fasteners can be applied to the proximal end of the cast for attachment to the connective means 2 to minimize twisting between the two braces. This limits the amount of unwanted forearm pronation or supination. During the final stage of patient rehabilitation, the cast can be replaced with, for example, the hand-wrist orthosis shown in FIG. 1. As such, the sugar tong forearm brace is designed to be used with different step down protocols depending on the injury and treatment protocol of the practitioner or physician.

While particular forms of the invention have been illustrated and described, it will be apparent that various modifications can be made without departing from the spirit and scope of the invention. It is contemplated that disclosed embodiments and their components may be combined with other disclosed embodiments and their components.

What is claimed is:

1. An elbow-forearm anti-rotation support system that does not include a hardenable material, comprising:
    an orthopedic support including a wrist-hand orthosis, wrist-hand-thumb orthosis, or cast;
    a clamshell forearm wrap having two opposed, first and second forearm flaps wrapped into a circumferential form, wherein the flaps approach each other, and wherein the wrap is wider at a distal end and narrower at a proximal end;
    proximal elbow flaps that join to the forearm wrap including an elbow portion pocket at a center region;
    first and second straps extending from the proximal elbow flaps and attachable to the first and second forearm flaps;
    a third strap extending from an edge of the first forearm flap and overlying where the first and second forearm flaps approach each other to join the opposed second forearm flap; and
    a means for connecting that extends from the distal end of the forearm wrap and is attached to the orthopedic support.

2. The elbow-forearm anti-rotation support system of claim 1, wherein the system includes a U-shaped reinforcement stay having a curved vertex and straight legs extending from the vertex, wherein the vertex is partially contained within the elbow portion pocket and the legs attach to the first and second forearm flaps.

3. The elbow-forearm anti-rotation support system of claim 2, wherein the U-shaped reinforcement stay includes an internal rigid strip.

4. The elbow-forearm anti-rotation support system of claim 1, wherein the first and second forearm flaps includes a plurality of semi-rigid panels.

5. The elbow-forearm anti-rotation support system of claim 1, wherein the first and second forearm flaps are discrete flaps joined along a common edge by a soft sheet of fabric.

6. The elbow-forearm anti-rotation support system of claim 1, wherein the elbow portion pocket is made from a soft fabric.

7. The elbow-forearm anti-rotation support system of claim 1, wherein at least one of the first and second forearm flaps includes an internal stiffener.

8. The elbow-forearm anti-rotation support system of claim 1, wherein the means for connecting includes a hook component of a hook and loop fastener.

9. The elbow-forearm anti-rotation support system of claim 1, wherein the first and second forearm flaps include padding, and further include unbroken loop material on an exterior.

10. A method for applying an elbow-forearm anti-rotation support system to a patient's thumb, wrist, forearm, or elbow, without use of a hardening material, comprising:
  applying an orthopedic support including at least one of a wrist cast, short arm cast, thumb spica cast, wrist-hand orthosis, or wrist-hand-thumb orthosis to the patient's thumb, wrist, forearm, or elbow;
  providing a clamshell forearm wrap with opposed first and second forearm flaps wrapped into a circumferential form wherein the flaps approach each other, and wherein the forearm wrap is wider at a distal end and narrower at a proximal end;
  embedding stiffeners into the forearm wrap;
  applying the forearm wrap to the patient's forearm;
  providing proximal elbow flaps with a center region at the proximal end of the forearm wrap, wherein the proximal flaps include first and second straps;
  inserting the patient's elbow into the center region;
  securing the first and second straps to the forearm wrap;
  providing a third strap, extending from the first to the second forearm flap;
  providing a means for connecting that extends from the distal edge of the forearm wrap; and
  attaching the means for connecting to the orthopedic support.

11. A method for applying an elbow-forearm anti-rotation support system to a patient's thumb, wrist, arm, or elbow, without use of a hardening material, wherein an orthopedic support has been applied to the patient's thumb, wrist, arm, or elbow, comprising:
  providing a clamshell forearm wrap with opposed first and second forearm flaps, wherein the flaps approach each other, and wherein the forearm wrap is wider at a distal end and narrower at a proximal end;
  embedding stiffeners into the forearm wrap;
  applying the forearm wrap to the patient's arm;
  providing first and second proximal elbow flaps with a center region at the proximal end of the forearm wrap, wherein the first and second elbow flaps include respective first and second straps;
  inserting the patient's elbow into the center region;
  securing the first and second straps to the forearm wrap;
  providing a third strap extending from the first to the second forearm flap;
  providing a means for connecting that extends from the distal end of the forearm wrap; and
  attaching the means for connecting to the orthopedic support.

12. An elbow-forearm anti-rotation support system that does not include a hardenable material for attachment to an orthopedic support including a wrist-hand orthosis, wrist-hand-thumb orthosis, or cast, comprising:
  a forearm wrap with two opposed, first and second forearm flaps, wherein the wrap includes a distal end and a proximal end;
  a plurality of stiffeners embedded within the forearm wrap;
  proximal elbow flaps with a center region that extends from the proximal end of the forearm wrap, wherein the center region includes an elbow portion, and the proximal elbow flaps include first and second straps attachable to the forearm wrap;
  a U-shaped reinforcement stay having a vertex and straight legs extending from the vertex, wherein the vertex is disposed on the elbow portion and the legs are disposed on the first and second forearm flaps;
  a third strap extending from the first forearm flap to the second forearm flap securing the two flaps together; and
  a means for connecting, extending from the distal end of the forearm wrap attachable to the orthopedic support.

13. The elbow-forearm anti-rotation support system of claim 12, wherein the forearm wrap further comprises a fourth strap at least partially disposed about a circumference of the forearm wrap.

14. The elbow-forearm anti-rotation support system of claim 12, wherein an exterior of the forearm wrap includes unbroken loop fabric.

15. The elbow-forearm anti-rotation support system of claim 12, wherein the forearm wrap includes laminated sheets of ethylene vinyl acetate foam (EVA) and unbroken loop (UBL) fabric.

16. The elbow-forearm anti-rotation support system of claim 12, wherein the means for connecting includes a hook component of a hook and loop fastener.

17. The elbow-forearm anti-rotation support system of claim 12, wherein the plurality of stiffeners embedded within the forearm wrap extend substantially the entire length of the forearm wrap.

* * * * *